(12) United States Patent
Berninger et al.

(10) Patent No.: US 9,095,568 B2
(45) Date of Patent: Aug. 4, 2015

(54) THERAPEUTIC AND VACCINE POLYELECTROLYTE NANOPARTICLE COMPOSITIONS

(76) Inventors: Mark Berninger, Gaithersburg, MD (US); Puthupparampil Scaria, Montgomery Village, MD (US)

( * ) Notice: Subject to any disclaimer, the term of this patent is extended or adjusted under 35 U.S.C. 154(b) by 1152 days.

(21) Appl. No.: 12/680,548

(22) PCT Filed: Sep. 26, 2008

(86) PCT No.: PCT/US2008/078021
§ 371 (c)(1),
(2), (4) Date: Oct. 6, 2010

(87) PCT Pub. No.: WO2009/079066
PCT Pub. Date: Jun. 25, 2009

(65) Prior Publication Data
US 2011/0014235 A1      Jan. 20, 2011

Related U.S. Application Data

(60) Provisional application No. 60/995,238, filed on Sep. 26, 2007.

(51) Int. Cl.
| | | |
|---|---|---|
| A61K 39/07 | (2006.01) | |
| A61K 39/00 | (2006.01) | |
| A61K 39/385 | (2006.01) | |
| A61K 47/00 | (2006.01) | |
| A01N 63/00 | (2006.01) | |
| A61K 39/39 | (2006.01) | |

(52) U.S. Cl.
CPC ....... *A61K 39/39* (2013.01); *A61K 2039/55555* (2013.01)

(58) Field of Classification Search
CPC .................... A61K 39/39; A61K 2039/55555; A61K 39/07; A61K 39/00
See application file for complete search history.

(56) References Cited

U.S. PATENT DOCUMENTS

| | | | | |
|---|---|---|---|---|
| 6,645,525 | B1 * | 11/2003 | Woiszwillo | 424/460 |
| 7,138,121 | B2 * | 11/2006 | Spangler et al. | 424/178.1 |
| 7,803,386 | B2 * | 9/2010 | Schneerson et al. | 424/234.1 |
| 2003/0166601 | A1 * | 9/2003 | Woodle et al. | 514/44 |
| 2004/0157330 | A1 * | 8/2004 | Sheridan et al. | 435/455 |
| 2007/0110786 | A1 * | 5/2007 | Tenney et al. | 424/423 |
| 2007/0154513 | A1 * | 7/2007 | Atanasoska et al. | 424/423 |
| 2010/0179645 | A1 * | 7/2010 | Chen et al. | 623/1.42 |

FOREIGN PATENT DOCUMENTS

WO    WO 2007/079193    *    7/2007

OTHER PUBLICATIONS

Kasturi et al., Biomaterials, 2005; 26(32): 6375-6385.*

* cited by examiner

*Primary Examiner* — Gary Nickol
*Assistant Examiner* — Lakia Tongue
(74) *Attorney, Agent, or Firm* — Perkins Coie LLC

(57) ABSTRACT

Polyelectrolyte nanoparticle compositions for biomedical applications are provided comprising at least two carrier domains comprising multivalent ionic domains and an agent exhibiting biological activity when contained within the nanoparticle or on the nanoparticle surface. The multivalent ionic domains may be contained in two separate molecules or in separate but linked domains of a single molecule. The nanoparticle optionally can further comprise an exposed targeting ligand and/or protective surface. The nanoparticle can be contacted to cells or administered directly to an animal for biomedical applications including therapeutics and immune response. The nanoparticle may alternatively be comprised of a carrier material capable of delivering various medically important antigens as vaccine.

7 Claims, No Drawings

THERAPEUTIC AND VACCINE POLYELECTROLYTE NANOPARTICLE COMPOSITIONS

This application is a 371 application of PCT/US2008/078021, filed Sep. 26, 2008, which claims priority to U.S. Provisional Application No. 60/995,238, filed Sep. 26, 2007, the contents of each of which are hereby incorporated by reference in their entireties.

FIELD OF THE INVENTION

The invention relates to nanoparticle for one or more molecules of interest, which can be contacted to cells or directly to an animal to produce a desired biological effect, where the nanoparticle contains at least two carrier materials with multivalent ionic moieties associated with an ionizable cargo. The invention relates to nanoparticles useful for biomedical applications including immunization and therapeutics. The invention further relates to nanoparticles comprising optionally one carrier material for the delivery of antigens as vaccines.

BACKGROUND OF THE INVENTION

A major need exists for new or improved vaccines including prophylactic vaccines for potential bioterrorism infectious organisms and therapeutic vaccines such as for cancer. For example, mailed powder containing anthrax material killed unsuspecting office workers and caused major disruption due, in part, to lack of a good and safe vaccine. The migration of avian flu is a major concern given lack of an effective vaccine. There exists a need for rapid development of vaccines toward emerging infectious agents such as SARS or bioterrorism developments. Therapeutic vaccines also are needed.

Anthrax is an infectious bacterial disease caused by *Bacillus anthracis* and occurs in domestic animals and humans exposed to infected animals, tissue, or spores. The virulence of *B. anthracis* is dependent on Anthrax Toxin (AT) and poly-gamma-D-glutamic acid capsule (PGA). PGA provides the bacteria a way to evade immune cells by providing a 'stealth' cover. PGA also is not very immunogenic. AT is composed of three entities: Protective Antigen (PA) (the binding subunit of AT), Lethal Factor (LF) and Edema Factor (EF) (Mikesell et al., Infect. Immun. 39:371-76, 1983; Vodkin et al Cell 34:693-97, 1983). PA is an 83 kDa protein that is the main protective constituent of anthrax vaccines. A currently approved human vaccine for Anthrax, which is manufactured from a cell free extract of un-capsulated *Bacillus Anthracis* (AVA, BioPort Corporation, Lansing Mich.), has several limitations including a requirement for six vaccinations over eighteen months followed by yearly boosters (Pittman et al., Vaccine 20:1412-20, 2002; Pittman et al., Vaccine 20:972-78, 2001) and is associated with undesirable reactions (Pittman et al., Vaccine 20:972-78, 2001). PA is necessary for vaccine immunogenicity (Ivins et al., Infect. Immun. 60:662-68, 199 Welkos and Friedlander, Microb. Pathog. 5:127, 1998) and can inhibit germination of spores (Welkos eta., Microbiology 147:1677-85, 2001). Current efforts for development of a new vaccine focus on using PA as the antigen. In order to have an effective prophylactic vaccine against capsulated bacteria and its toxin, a combined immune response against PA and the PGA will be advantageous. Late stage clinical development by VaxGen of an experimental vaccine based on recombinant PA has been put on hold.

Anthrax toxins are formed by PA, lethal factor (LF), and edema factor (EF), which are secreted separately as nontoxic monomers. Binding of LF or EF to PA produces active toxin. PA along with bound LF or EF is internalized by cells by receptor mediated endocytosis in a heptameric form. In the endosome, PA undergoes a pH-induced conformational change, producing a pore in the endosomal membrane permitting toxin translocation into the cytoplasm and toxicity. The conjugation of PA to gamma-D-PGA has been suggested as a means to obtain simultaneous immune responses (Rhie et al. PNAS 100, 10925 2003, Schneerson et al. WO 2005/000884). Antigenic constructs that can provide presentation of PA and PGA to antigen presenting cells and also prevent the multimerization and pore formation of PA molecules, will be advantageous in preventing the infection and the effect of toxin.

Many viral infections are not managed adequately, requiring new or better vaccines, including avian flu. The major viral antigens of influenza, including N, HA, and M proteins, change rapidly, limiting the benefit of each vaccine. Also current production relies on growth in eggs with severe commercial limitations. An effective and safe vaccine not dependent on biological manufacturing and that is rapidly adaptable for rapidly changing antigens is needed.

The purpose of a therapeutic vaccine is not only to induce an immune response but to induce a response that is beneficial for patients already exposed to an infectious agent or who have ongoing infection or disease. One major interest for potential application of therapeutic vaccines is for treatment of cancer patients. However, commercially successful products have encountered several hurdles, including the difficulty of identifying antigens, finding antigens that are broadly applicable, and identifying adjuvants that achieve an effective immune response. Despite the recent achievements using nanoparticles to improve immune response, a need clearly exists for more effective and safe prophylactic and therapeutic vaccines as well as further improvements in nanoparticles to address needed capabilities.

Most candidate therapeutic classes, from large proteins such as antibodies, to small molecules such as chemotherapy, are limited by pharmacological barriers that potentially can be overcome using drug delivery. Production of pharmaceutically active polypeptides and nucleic acids is adequate (Biomacromolecules 2004; 5:1917-1925), but their use remains limited by many barriers, including absorption, diffusion into cells, degradation, etc. (J. Control. Release 1996; 39:131-138). Small molecules also can face similar barriers, such as toxicity from widespread biodistribution, and these severely limit their development as seen by annual decreases in new drug approvals even though delivery systems often are incorporated. Another growing clinical need is for combinations of approved products, again pointing to a need for better delivery systems with capabilities for two or more active ingredients.

Nanoparticles have benefited several commercialized therapeutics, but the extensive research revealed numerous barriers and challenges hampering further application. Major challenges include a need for better manufacturing, control of particle size and homogeneity, cargo loading, cargo release at the target cell or tissue, biocompatibility, and disease selectivity. Improvement is needed for broad commercial application.

Hydrophilic polymer conjugates of active ingredients to improve pharmacological activity have been reported. These materials are nanoscale but are soluble and thus are not nanoparticles. Commercialization limitations include a need for all functions, such as targeting ligands, to be coupled effectively to the large carrier and difficulty for the carrier to meet all the strict regulations applied to the active ingredient, exacerbated as the carrier size increases. Adaptation of hydrophilic carriers for use in nanoparticles has been disclosed frequently by conjugation with poorly soluble material such as lipids, polylactides, etc., and further comprising association of active ingredient either covalently or non-covalently. In this case the conjugate forms or associates with a micelle, liposome, or solid colloid. A limitation of such compositions is that to obtain the nanoparticle benefits, the carrier mass and components is increased, reducing commercial utility due to increased costs, lower drug loading, great product heterogeneity. Although development of nanoparticles has led to improved products, the current compositions fail to address the needs of many vaccine and therapeutic applications. Therefore, a need exists for effective and safe vaccines and therapeutics.

SUMMARY OF THE INVENTION

The invention provides polyelectrolyte nanoparticles comprising charged carriers or carrier domains in a complex with a cargo. The nanoparticle optionally can further comprise targeting ligands and/or a protective surface. The nanoparticle can be contacted to cells or administered directly to an animal for biomedical applications including vaccination and delivery of therapeutics. One embodiment of the invention relates to prophylactic vaccines for infectious agents including *Bacillus anthracis*, avian influenza, and other potential "bioterrorism" organisms. Another embodiment relates to therapeutic vaccines for disease including DNA cancer vaccines. Yet another embodiment relates to therapeutics including antiangiogenic and anticancer treatments including squalamine, mitomycin C, and mitoxantrone.

DETAILED DESCRIPTION OF THE INVENTION

The invention provides polyelectrolyte nanoparticles comprising at least two carrier molecules or two separate domains of a single molecule comprising ionizable moieties or domains of moieties or at least one multivalent charged domain with sufficient size, shape and charge to form complexes with a charged or zwitterionic cargo, preferably multivalent charge. A cargo is defined herein as a molecule that is biologically active following delivery by a delivery material or method to an intended cell.

Nanoparticles can be formed from interactions between the carrier materials or carrier domains and between the carriers or carrier domains and the cargo. Carrier materials or carrier domains can be comprised of oppositely charged domains. In a preferred embodiment, a carrier or carrier domain is substantially homogenous in charge. Carrier can be a single material having separate but linked oppositely charged domains, preferably where the linkage allows the two domains to freely move one another to associate with other domains or with the cargo. Largely independently of the ratio of materials forming the nanoparticle, the interior of the nanoparticle comprises polyelectrolyte complexes of nearly equal charge ratio and largely lacking solvent Net surface charge of the nanoparticle is substantially determined by ratio of carrier to cargo, the ionization state of surface moieties, etc. and can be influenced by adsorbed ions, and polymers, The net surface charge can therefore be adjusted by modifying the above parameters. The nanoparticle preferably has a net surface charge which may be either positive or negative.

Nanoparticles can comprise an anionic carrier or domain and a cationic carrier or domain with cationic or anionic cargo, or vice versa. A nanoparticle may contain more than one cargo and the different cargos may either be anionic or cationic. The same nanoparticle may contain both an anionic and a cationic cargo. A large range of ionizable cargo materials can be used, including bacterial surface components, poly-gamma-D-glutamate, toxins, antigens, viral surface antigens, phosphorylated molecules, nucleic acids, anionic peptides, cationic peptides, polyamines, inhibitors of polyamine pools, squalamine, polyamine sterols, and cationic anticancer agents including mitoxantrone. A nucleic acid may comprise a sequence for expression and may comprise a sequence inhibiting expression of genes including RNA or expression of RNA including antisense and RNAi factors. The nucleic acid of the invention may comprise chemical analogues.

The nanoparticle preferably comprises biocompatible, or preferably biodegradable, carrier materials. The biocompatible carrier of the invention reduces non-specific toxicity and biodegradable carrier can be degraded into components of cellular metabolism or excreted. The nanoparticle preferably is degraded or disassembles during its biomedical application, permitting desired cargo biological activity and permitting carrier material to be metabolized and/or excreted. Nanoparticle disassembly can be achieved by selection of carrier material comprising moieties with a range of binding affinities with the cargo from weak to strong where the affinity selected within that range permits nanoparticle disassembly, or whose affinity is reduced response to biological conditions. The selection of the bio-responsive moieties or groups depends on the chemical or structural nature of the moieties of the cargo and the biological compartment where disassembly is desired.

The nanoparticle may further comprise a second carrier domain opposite in charge to the first carrier. The second carrier material preferably exhibits weaker affinity with the first carrier than with the cargo during nanoparticle formation and storage, and optionally can undergo a change to stronger affinity so as to facilitate release of cargo from the nanoparticle.

The nanoparticle may further comprise additional cargo materials and/or biological modifiers. The nanoparticle of the invention may comprise two or more "active ingredients", for applications when their simultaneous activity is desired, for example antibody responses against multiple antigens or inhibition of redundant biochemical pathways. The nanoparticle optionally may further comprise one or more biological modifiers including surface exposed targeting ligand, encapsulated ligand, adjuvant, intracellular binding motif, bio-responsive material or moieties such as membrane fusing agent, membrane penetrating agent, pH or redox labile or responsive moieties, and protective coating.

The invention provides for vaccines for the prevention and treatment of infection. In this embodiment, the invention provides for 1) in vivo administration of nanoparticles of the invention including local administration or 2) ex-vivo treatment including application of nanoparticles of the invention to antigen presenting cells in culture. In this embodiment, the nanoparticles of the invention preferably have an average particle size of about 0.1 micron to about 1 micron. For local in vivo administration, the nanoparticles of this embodiment preferably have an average particle size of about 0.2 micron to about 1 micron. For systemic in vivo administration, the nanoparticles of this embodiment preferably have an average particle size of about 0.1 micron to about 0.2 micron. For ex-vivo administration, the nanoparticles of this embodiment preferably have an average particle size of about 0.2 micron to about 1 micron. Nanoparticles with an average particle size of about 1 micron are advantageously used in cell culture to contact adherent cells. Nanoparticles with an average particle size of no more than about 0.2 micron are advantageously produced with sterilization by terminal filtration. Nanoparticles of the invention optionally can be contacted with cells in culture with the aid of centrifugation or other means to facilitate cell contact.

In this embodiment, the nanoparticle comprises only a cationic carrier and an antigen. The cationic carrier may be selected from a wide range of material including a lipid, polyamine, polyimine, dendrimer, or polypeptide. The carrier may be a cationic derivatized polyaspartate or polyglutamate, including modified polyasparagine or polyglutamine. The carrier preferably comprises a cationic polypeptide and optionally may comprise about 10 to 100% lysine, preferably with a size of about 1,000 to 50,000 daltons, and may be linear or preferably comprises branching of about 10 to 100% of the amino acid residues. The carrier preferably comprises a "dendrimer" polypeptide formed using lysine based branching. The preferred embodiment comprises antigen of about 1,000 to about 100,000 Molecular Weight (MW), preferably about 1,000 to about 10,000 MW. The nanoparticle optionally further comprises an adjuvant. The adjuvant may be selected from a wide range of material including inulin, a "CpG" oligonucleotide, and lipopolysaccharide. The embodiment may further comprise unbound materials including adjuvant. In this embodiment, the invention provides for airway administration including nasal spray and aerosol inhalation. In this embodiment, the invention provides for an initial "prime" application followed by at least one "boost" application and in a preferred embodiment subsequent "boost" administration less frequently than once a year.

In one specific embodiment, the nanoparticle comprises a cationic carrier and an antigen comprising poly-gamma-D-glutamate (gamma-D-PGA). The carrier optionally comprises a biodegradable polycation and preferably comprises a lysine rich polypeptide. The nanoparticle of this embodiment preferably comprises low surface exposure of PGA. The nanoparticle of this embodiment preferably further comprises an antigenic portion of anthrax "protective antigen" (PA) and optionally may comprise surface exposure of PA. In a preferred embodiment the nanoparticle optionally comprises both PA and PGA and may further comprise PA chemically coupled to PGA. The nanoparticle optionally comprises an adjuvant and preferably a "CpG" oligonucleotide and optionally may comprise, in a preferred embodiment, the CpG covalently coupled to the PGA antigen. In this embodiment, the nanoparticle is administered by subcutaneous injection, intravenous injection and preferably by airway administration including nasal spray and aerosol inhalation.

The invention provides for therapeutic vaccines in the treatment of chronic infection or disease lasting longer than the time to achieve an adequate immune response, often at least two weeks. In this embodiment, the invention provides for antigen in a wide range of forms including polypeptide, polysaccharide, and nucleic acid. Optionally, the nucleic acid may comprise a sequence for expression or for inhibiting expression and optionally comprises sequences of RNA or expression of RNA including antisense factors. The nucleic acid of the invention optionally may comprise chemical analogues.

In a specific embodiment, the nanoparticle of the invention comprises an ionic carrier and an antigenic polypeptide. In a preferred embodiment, the antigen comprises at least one tumor antigen and in a preferred embodiment comprises at least two different tumor antigens. The tumor antigen or antigens may be selected from proteins selectively expressed by tumors, such as HER2 and 5T4, and/or selectively exposed on the surface of tumor cells, such as gp96 or other human tumor antigens recognized by T cells can be used as antigens in the invention. In one specific embodiment the invention comprises antigenic sequences from the extracellular domain of HER2 and optionally further comprises antigenic sequences of MUC-1. The antigen optionally further comprises a calreticulin polypeptide exhibiting immune stimulation activity. The carrier preferably comprises a cationic carrier, and optionally is the same carrier provided for by embodiments for prophylactic anthrax vaccines. The preferred embodiment comprises antigen of at least about 10,000 MW. The nanoparticle of this embodiment preferably lacks surface exposure of PGA and optionally preferably lacks a protective surface. A preferred embodiment of the invention optionally further comprises surface exposure of anthrax PA sufficiently to permit binding to antigen presenting cells.

In yet another specific embodiment, the nanoparticle comprises a cationic carrier and a nucleic acid. The cationic carrier preferably lacks arginine and guanidinium and has endosomolytic property. The carrier optionally may be a carrier provided for by embodiments of the invention for prophylactic anthrax vaccines. The cationic carrier preferably is rich in histidine, imidazole, lysine, and amines, and preferably comprises branched structure. The cationic carrier may be linear or branched PEI, preferably large linear PEI or small branched PEI. The cationic carrier may comprise a lysine-rich polypeptide, preferably branched with at least 50% of the cationic ionizable groups comprising histidine or imidazole. The nanoparticle optionally comprises a hydrophilic polymer exposed on the surface and/or comprises an exposed ligand for antigen presenting cells. The hydrophilic polymer, when present, is preferably PEG. The exposed ligand, when present, is preferably a polypeptide and more preferably comprises an APC binding portion of anthrax protective antigen or comprises an RGD peptide. The nucleic acid may comprise a sequence for expression and optionally comprises sequences of antiangiogenic factors, tumor antigens, immune stimulatory factors. In a preferred embodiment, the nucleic acid comprises sequences of multiple factors. The nucleic acid may comprise single or multiple expression cassettes. In a preferred embodiment, the nucleic acid comprises sequences of at least one tumor antigen and sequences of GM-CSF, and optionally further comprises sequences of at least one tumor antigen fused to a calreticulin sequence exhibiting immune stimulation and/or antiangiogenic activity. The nanoparticle of this embodiment optionally may further comprise surface exposure of anthrax PA.

The invention provides for therapeutic treatment of disease. In this embodiment, the invention provides for in vivo administration of nanoparticles of the invention including local or systemic administration. In this embodiment, the nanoparticles of the invention preferably have an average particle size less than about 0.2 micron.

In a specific embodiment, the nanoparticle comprises a cargo associated with an ionic carrier and preferably comprises an anionic carrier. The carrier may be synthetic or of bacterial or mammalian origin, including hyaluronate, chitin, heparin sulfate, and polyglutamate. In one preferred embodiment, the carrier comprises a poly-glutamate polymer (PGA). A PGA polymer of this embodiment is preferably about 2,000 to about 300,000 daltons and more preferably of about 5,000 to about 100,000 daltons. A PGA carrier may be linear or preferably comprises a branched structure. The nanoparticle of this embodiment optionally further comprises PGA exposed on the surface and preferably comprises a protective PGA surface layer. The nanoparticle of this embodiment may further comprise a second carrier material. In this embodiment, the cargo optionally is coupled to the carrier. Coupled cargo may be cationic, anionic, or neutral/zwitterionic. The cargo may comprise at least one cationic moiety, and preferably multiple cationic moieties. A nanoparticle of this embodiment may comprise a carrier electrostatically associated with a cationic cargo including a peptide, polyamine, inhibitor of polyamine pools, squalamine, polyamine sterol, and cationic anticancer agent including mitoxantrone. Cargo coupling may be non-covalent or optionally may be covalent. When cargo association with carrier by non-covalent coupling is insufficient to maintain association during storage a covalent coupling is preferred. Coupling to a cargo moiety can include coupling via an amine, alcohol, aldehyde or carboxylic acid. In a preferred embodiment the coupling is reversible and optionally the coupling can provide tissue selective release. A preferred embodiment provides coupling with a dithiol benzyl that exhibits reduction mediated release, one form of which was disclosed by Zalipsky (See U.S. Pat. No. 7,238,368) for 1) coupling to some non-ionic polymers (but lacking any teaching for use with ionic polymers including PGA) and 2) methods to determine release. In a preferred embodiment, a nanoparticle comprises branched PGA and squalamine and optionally further comprises a nanoparticle forming material with reduced water solubility such as a lipid or a polymer.

In a specific embodiment, the nanoparticle comprises squalamine. In this embodiment the nanoparticle has a squalamine content from about 1% to about 30% w/w and optionally comprises a ratio of PGA charge to squalamine charge from about 1:2 to about 10:1 and preferably from about 1:1.5 to about 5:1.

In another preferred embodiment, the cargo comprises at least one chemotherapeutic agent. In this latter embodiment, the cargo comprises mitomycin C and optionally comprises a linkage to an amine.

In another preferred embodiment, the cargo comprises at least two agents. In a specific embodiment, the cargo comprises mitomycin C and squalamine. In this embodiment the nanoparticle comprises a mitomycin C to squalamine ratio from about 3:1 to about 1:10 and preferably from about 1.5:1 to about 5:1.

The invention provides nanoparticle compositions for ex-vivo treatment including application to antigen presenting cell culture. In this embodiment, the nanoparticles of the invention preferably have an average particle size of about 0.2 micron to about 1 micron.

The invention provides nanoparticle compositions for ex-vivo treatment including application to immune cell culture including b-cell and t-cell culture. In this embodiment, the nanoparticles of the invention preferably have an average particle size of about 0.2 micron to about 1 micron.

Example 1

Conjugation of Protective Antigen (PA) of *Bacillus Antharacis* with Poly-Gamma-D-Glumatic Acid (PGA)

Recombinant PA is produced in bacteria culture by fermentation of *E-Coli* expressing a plasmid encoding the PA. The expressed protein is purified by standard chromatographic techniques. PGA is prepared from *Bacillus Licheniformis* or *Bacillus subtilis* according to the procedures described in Perez-Camero, G. et al, Biotechnol. Bioeng. 63, 110 (1999) or Kuboto, H et al, Biosci Biotech Biochem, 57, 1212 (1993). Sonication is used to reduce the molecular weight of the polymer.

Conjugation of the PA molecule to PGA is carried out using standard coupling agents, such as water soluble EDC, 1-ethyl-3-(3-dimethylaminopropyl)carbodiimide hydrochloride which couples the carboxylic acid of PGA to the PA protein by formation of an amide bond. Other standard coupling reagents also can also be used to prepare a substantially equivalent conjugate. The resulting conjugates are purified by standard column chromatography and characterized by Mass Spectrometry.

Example 2

Preparation of Nanoparticle Comprising the PA-PGA Conjugate

Nanoparticle comprising the PA-PGA conjugate is prepared by combining and mixing the poly-anionic PGA moiety with a poly-cationic material such as poly-lysine, polyethyleneimine, Histidine-Lysine co-polymers, or Histidine and Lysine containing linear or branched peptides, to effect the self-assembly of the nanoparticle. A solution containing PA-PGA conjugate is mixed with a solution containing a polycation to form nanoparticles. Mixing is carried out by simple addition of the solution giving excess charge ratio to the other, followed by vortexing of the combined solutions, or by using a static mixer where the two solutions are pumped into a static mixer to be mixed within the helical mixing element of a static mixer. Electrostatic interaction between the anionic PGA with the polycation lead to self assembly and formation of nanoparticles. The molar ratio of PGA to polycation may be adjusted to obtain particles with net negative, neutral or positive surface charge. Particles with net surface charge will provide increased colloidal stability to the nanoparticle formulation. In order to further enhance stability, surfactants optionally will be added to one or both of the solutions. Samples may be prepared with added pluronic surfactant. Nanoparticle samples may be prepared so that some of the PA molecules are exposed on the surface of the particle to facilitate the uptake of the particle by antigen presenting cells and thereby elicit an immune response against PA and PGA.

Example 3

Chemical Synthesis of Gamma-D-Glutamic Acid Oligomeric Peptides (GDGP) and their Conjugation to PA Peptides containing from 10 to 15 consecutive D-Glu residues coupled through the gamma carboxylic acid of the side chain to the alpha amino group of the neighboring C-terminal residue are synthesized by solid phase synthesis using D-Glu derivatives. 3 to 5 amino acid residues of Gly, Serine, Lysine, Ala or beta-alanine are incorporated into the N-terminus of the peptide to provide conjugation site through the alpha-amine, as well as to provide spacing between the D-Glu block and the conjugated protein. To enable conjugation through a sulfhydryl group, a Cys residue is incorporated at the N-terminus of the peptide. The synthesized peptide is purified by HPLC and characterized by MALDI.

Conjugation of Gamma-D-Glutamic Acid Oligopeptide (GDGP) to PA.

D-Glu peptides containing Cys at the N terminus are coupled to the Protein (PA) through a sulfhydryl containing side-chain. The protein in aqueous solution at pH between 7 and 8 is reacted with sulfosuccinimidyl-4-(N-maleimidomethyl)cyclohexane-1-carboxylate (Sulfo-SMCC). The maleimide activated protein is purified using a desalting column to remove excess sulfo-SMCC. To the purified protein conjugate, Cys containing peptide is added and the pH is adjusted to between 6.6 and 7.5. The maleimide coupling with the —SH group of the Cys side chain yields a PA-peptide conjugate which is further purified by standard column chromatography. The conjugate is characterized by Mass Spectrometry to determine the number of peptide molecules coupled to the PA molecule.

A similar coupling procedure is used to couple the N-terminus amine of the peptide to PA amines. In this case, first the peptide is reacted with an excess (2-3 molar excess) of a homobifunctional cross linker, DSG (disuccinimidyl glutarate) under anhydrous conditions. The reaction is carried out in dry DMSO or DMF in the presence of 1-2 equivalents of base. NHS ester reacts with the N-terminal amino group of the peptide. Once the reaction is complete, the derivitized peptide is precipitated using dry ether and the solid material recovered and stored under anhydrous condition. This peptide with a NHS active terminus is used in a subsequent step to react with PA in aqueous buffer, pH 7-8, to prepare the conjugate of PA-peptide. This conjugate is purified by column chromatography and characterized by Mass Spectrometry. The number of peptides conjugated per PA molecule is determined by Mass Spectrometry.

Preparation of Nanoparticle Comprising the PA-GDGP Conjugates:

Nanoparticle comprising the PA-GDGP conjugates is prepared by the self-assembly of the poly-anionic GDGP moiety with a poly-cationic material such as poly-lysine, polyethyleneimine, Histidine-Lysine co-polymers, or Histidine and Lysine containing linear or branched peptides. A solution containing PA-GDGP conjugate is mixed with a solution containing a polycation to form nanoparticles. Mixing is carried out by simple addition of the solution giving excess charge ratio to the other followed by vortex, or using a static mixer where the two solutions are pumped into a static mixer to be mixed within the helical mixing element of a static mixer. Electrostatic interaction between the anionic GDGP with the polycation leads to self assembly of particles. The molar ratio of GDGP to polycation is adjusted to obtain particles with net negative, neutral or positive surface charge. Particles with net surface charge provide colloidal stability to the nanoparticle formulation. In order to further enhance the stability, surfactants optionally are added to one or both solutions. Samples are prepared with pluronic surfactant (Sigma). Nanoparticle samples are prepared so that some of the PA molecules are exposed on the surface of the particle, to facilitate the uptake of the particle by antigen presenting cells to elicit an immune response against PA and GDGP.

Example 4

Synthesis of Branched Gamma-D-Glutamic Acid (bGDGP) and its Conjugation to PA

Branched peptides with 2 or more arms, with each arm consisting of peptides containing 10 and 15 consecutive D-Glu residues coupled through the gamma carboxylic acid of the side chain to the alpha amino group of the neighboring C-terminal reside are synthesized by solid phase synthesis using D-Glu derivatives. 3 to 5 amino acid residues of Gly, Ala or beta-alanine are incorporated into the C-terminus terminus of the sequence to provide spacing between the D-Glu block and the conjugated protein. To enable conjugation through a sulfhydryl group, a Cys residue also may be incorporated at the C-terminus of the peptide. Branching is introduced by incorporation of Lysine residues in the sequence N-terminal to the spacer amino acids. Insertion of one Lys in the linear sequence can provide a branching point since further addition of amino acid residues can proceed through both α and ε amino groups of the Lys residue. A second Lys coupling can increase the number of branches to 4. The G-Glu derivatives can then be coupled to the 4 branches simultaneously through the activated gamma carboxylic acid, to generate the branched peptide. The synthesized peptide is purified by HPLC and characterized by MALDI.

Conjugation of Gamma-D-Glutamic Acid Oligopeptide (bGDGP) to PA:

bGDGP containing Cys at the C terminus is coupled to the Protein (PA) through the sulfhydryl side-chain of Cys and amino groups on the PA. Briefly, the protein in aqueous solution of pH between 7 and 8 is reacted with sulfosuccinimidyl-4-(N-maleimidomethyl)cyclohexane-1-carboxylate (Sulfo-SMCC). The succinimidyl group reacts with amino group on the protein to form a stable amide bond. The maleimide-activated protein is purified by a desalting column to remove excess sulfo-SMCC. To the purified protein conjugate, Cys containing peptide is added and the pH is adjusted to between 6.5 and 7.5. The maleimide coupling with the —SH group of the Cys side chain yields a PA-bGDGP conjugate which is further purified by column chromatography. The conjugate is characterized by Mass Spectrometry to determine the number of peptide molecules coupled to the PA molecule.

Preparation of Nanoparticle Comprising the PA-bGDGP Conjugates:

Nanoparticle comprising the PA-bGDGP conjugates is prepared by the self-assembly of the poly-anionic GDGP moiety with a poly-cationic material such as poly-lysine, polyethyleneimine, Histidine-Lysine co-polymers, or Histidine and Lysine containing linear or branched peptides. A solution containing PA-GDGP conjugate is mixed with a solution containing a polycation to form nanoparticles. Mixing is carried out by simple addition of one solution to the other followed by vortex or using a static mixer, where the two solutions are pumped into a static mixer to be mixed within the helical mixing element of a static mixer. Electrostatic interaction between the anionic bGDGP with the polycation leads to the formation of particles. The molar ratio of bGDGP to polycation is adjusted to obtain particles with net negative, neutral or positive surface charge. Particles with net surface charge provide colloidal stability to the nanoparticle formulation. In order to further enhance the stability, surfactants optionally are added to one or both solutions. Samples are prepared with pluronic surfactant. Nanoparticle samples are prepared so that some of the PA molecules are exposed on the surface of the particle, to facilitate the uptake of the particle by antigen presenting cells to elicit an immune response against PA and bGDGP.

Example 5

Preparation of Nanoparticle Comprising HK Polymer and PGA Polymer

Nanoparticle comprising HK polypeptide polymers and PGA is prepared by self-assembly of the poly-anionic PGA moiety with a poly-cationic Histidine-Lysine co-polymers of linear or branched form. A solution containing PGA is mixed with a solution containing HK polymer to form nanoparticles. Mixing is carried out by simple addition of the solution giving excess charge ratio to the other followed by vortex, or using a static mixer where the two solutions are pumped into a static mixer to be mixed within the helical mixing element of a static mixer. Electrostatic interaction between the anionic PGA with the polycation lead to self assembly of particles. The molar ratio of PGA to polycation is adjusted to obtain particles with net negative, neutral or positive surface charge. Particles with net surface charge provide colloidal stability to the nanoparticle formulation. In order to further enhance the stability, surfactants optionally are added to one or both solutions. Samples are prepared with pluronic surfactant. Nanoparticle samples are prepared so that some of the PGA molecules are exposed on the surface of the particle, to protect the nanoparticle from phagocytic cell uptake.

Example 6

Preparation of Nanoparticle Comprising Squalamine and PGA

Nanoparticles comprising cationic Squalamine are prepared by self assembly of Squalamine poly-anionic GDGP, bGDGP or PGA. A solution containing Squalamine is mixed with a solution containing a polyanion to form nanoparticles. Mixing is carried out by simple addition of one solution to the other followed by vortex or using a static mixer, where the two solutions are pumped into a static mixer to be mixed within the helical mixing element of a static mixer. Electrostatic interaction between the anionic glutamic acid with the cationic Squalamine leads to the formation of particles. The molar ratio of polyanionic species to Squalamine is adjusted to obtain particles with net negative, neutral or positive surface charge. Particles with net surface charge provide colloidal stability to the nanoparticle formulation. In order to further enhance the stability, surfactants or hydrophilic polymers such as PEG are incorporated into the nanoparticle through covalent bonding or by non-covalent interaction.

Example 7

Preparation of Nanoparticle Comprising Squalamine Conjugated to Cationic Polypeptide The amino group of Squalamine is conjugated to cationic polypeptides consisting Lys, or His and Lys amino acids through using homobifunctional cross linkers described in Example 3, or through coupling with a dithiol benzyl that exhibits reduction mediated release of Squalamine as described in U.S. Pat. No. 7,238,368 which is herein incorporated by reference.

The Squalamine-Polycation conjugate is mixed with PGA, GDGP or bGDGP to form nanoparticles. Mixing is carried out by simple addition of one solution to the other followed by vortex or using a static mixer, where the two solutions are pumped into a static mixer to be mixed within the helical mixing element of a static mixer. Electrostatic interaction between the anionic glutamic acid with the cationic Squalamine-polycation conjugate leads to the formation of particles. The molar ratio of polyanionic species to Squalamine-polycation conjugate is adjusted to obtain particles with net negative, neutral or positive surface charge. Particles with net surface charge provide colloidal stability to the nanoparticle formulation. In order to further enhance the stability, surfactants or hydrophilic polymers such as PEG are incorporated into the nanoparticle through covalent bonding or by non-covalent interaction.

The invention claimed is:

1. A nanoparticle comprising:
a first polyvalent carrier domain wherein the first polyvalent carrier domain is made up of more positively ionizable moieties than negatively ionizable moieties,
a second polyvalent carrier domain wherein the second polyvalent carrier domain is made up of more negatively ionizable moieties than positively ionizable moieties,
wherein the first and second polyvalent carrier domain comprises a polyamide, polysaccharide, polyacetal, polyester, polyamine, polyallylamine, polyimine, polyethyleneimine, or aminodextran;
and an ionizable biologically active agent covalently coupled to the first or second polyvalent carrier domain;
wherein said biologically active agent comprises an antigen, a chemotherapeutic agent, or a nucleic acid;
wherein said nanoparticle has an average size from about 0.1 to about 1.0 micron; and
wherein the first polyvalent carrier domain comprises biocompatible material;
provided by metabolic degradation or excretion and
wherein said first polyvalent carrier domain has a molecular weight of less than about 20,000 Daltons.

2. The nanoparticle of claim 1, wherein the first and second polyvalent carrier domains are present on two separate molecules.

3. The nanoparticle of claim 1, wherein the first or second polyvalent carrier domain comprises at least about 10% monomers capable of forming a branch.

4. The nanoparticle of claim 1, wherein the antigen comprises an antigenic component of an infectious organism or infectious agent.

5. A composition comprising the nanoparticle according to claim 1, in a pharmaceutically acceptable formulation.

6. A nanoparticle comprising:
a first polyvalent carrier domain wherein the first polyvalent carrier domain is made up of more positively ionizable moieties than negatively ionizable moieties,
a second polyvalent carrier domain wherein the second polyvalent carrier domain is made up of more negatively ionizable moieties than positively ionizable moieties,
wherein the first and second polyvalent carrier domain comprises a polyester;
and an ionizable biologically active agent covalently coupled to the first or second polyvalent carrier domain;
wherein said biologically active agent comprises an antigen, a chemotherapeutic agent, or a nucleic acid;
wherein said nanoparticle has an average size from about 0.1 to about 1.0 micron; and
wherein the polyester is selected from the group consisting of a polyserine, and polythreonine polyester.

7. A nanoparticle comprising:
a first polyvalent carrier domain wherein the first polyvalent carrier domain is made up of more positively ionizable moieties than negatively ionizable moieties,
a second polyvalent carrier domain wherein the second polyvalent carrier domain is made up of more negatively ionizable moieties than positively ionizable moieties,
wherein the first and second polyvalent carrier domain comprises a polyamide, polysaccharide, polyacetal, polyester, polyamine, polyallylamine, polyimine, polyethyleneimine, or aminodextran;
and an ionizable biologically active agent covalently coupled to or associated with the first or second polyvalent carrier domain;
wherein said biologically active agent comprises an antigen, a chemotherapeutic agent, or a nucleic acid;

wherein said nanoparticle has an average size from about 0.1 to about 1.0 micron;
wherein the antigen comprises an antigenic sequence of anthrax protective antigen; and
wherein the particle further comprises a second antigen comprising poly-gamma-D-glutamic acid of at least 3 monomers in length and wherein the composition lacks exposed polyglutamic acid.

* * * * *